United States Patent
Joerger et al.

(10) Patent No.: US 10,779,774 B2
(45) Date of Patent: Sep. 22, 2020

(54) METHOD AND APPARATUS FOR ENSURING CORRECT POSITIONING FOR A RADIOGRAPHY ACQUISITION

(71) Applicant: Siemens Healthcare GmbH, Erlangen (DE)

(72) Inventors: Clemens Joerger, Forchheim (DE); Ralf Nanke, Neunkirchen am Brand (DE); Susanne Oepping, Erlangen (DE)

(73) Assignee: Siemens Healthcare GMBH, Erlangen (DE)

(*) Notice: Subject to any disclaimer, the term of this patent is extended or adjusted under 35 U.S.C. 154(b) by 0 days.

(21) Appl. No.: 16/223,286

(22) Filed: Dec. 18, 2018

(65) Prior Publication Data

US 2019/0183439 A1 Jun. 20, 2019

(30) Foreign Application Priority Data

Dec. 20, 2017 (EP) .................................. 17209022

(51) Int. Cl.
*A61B 6/08* (2006.01)
*G06T 17/00* (2006.01)
(Continued)

(52) U.S. Cl.
CPC .............. *A61B 6/08* (2013.01); *A61B 5/0064* (2013.01); *A61B 6/04* (2013.01); *A61B 6/0457* (2013.01);
(Continued)

(58) Field of Classification Search
CPC ....... A61B 6/08; A61B 5/0064; A61B 6/0457; A61B 6/469; A61B 6/544; A61B 6/54;
(Continued)

(56) References Cited

U.S. PATENT DOCUMENTS 8,730,314 B2 * 5/2014 Hannibal ............. A61N 5/1048
348/77
10,154,239 B2 * 12/2018 Casas ................... H04N 13/279
(Continued)

FOREIGN PATENT DOCUMENTS

DE 10250571 A1 7/2003
DE 102012201798 A1 8/2013
(Continued)

OTHER PUBLICATIONS

European Search Report for Patent Application No. EP 17209022.7 dated Jul. 12, 2018.
(Continued)

*Primary Examiner* — Kiho Kim
(74) *Attorney, Agent, or Firm* — Harness, Dickey & Pierce, P.L.C.

(57) ABSTRACT

A method for positioning a body region of a patient for a radiography acquisition by a radiography system includes providing an examination requirement for the body region, pre-positioning the body region in the radiography system for the radiography acquisition, pre-positioning an acquisition unit of the radiography system for the radiography acquisition, producing a three-dimensional positioning acquisition of the body region using a 3D camera system, and producing a preview image from the three-dimensional positioning acquisition. A patient model is generated from the three-dimensional positioning acquisition and the preview image is produced from the patient model, and the preview image depicts a representation as if made using the acquisition unit of the radiography system. The method further includes outputting at least one of the preview image and positioning information based on the preview image. Another embodiment may use an apparatus and computer readable medium to execute the method above.

19 Claims, 3 Drawing Sheets

(51) Int. Cl.
*G06T 7/292* (2017.01)
*A61B 6/00* (2006.01)
*A61B 5/00* (2006.01)
*A61B 6/04* (2006.01)
*G03B 42/02* (2006.01)

(52) U.S. Cl.
CPC .............. *A61B 6/467* (2013.01); *A61B 6/469* (2013.01); *A61B 6/488* (2013.01); *A61B 6/54* (2013.01); *A61B 6/544* (2013.01); *A61B 6/545* (2013.01); *G03B 42/026* (2013.01); *G06T 7/292* (2017.01); *G06T 17/00* (2013.01); *G06T 2207/20081* (2013.01); *G06T 2210/41* (2013.01)

(58) Field of Classification Search
CPC ........... A61B 6/467; A61B 6/488; A61B 6/04; G06T 17/00; G06T 7/292; G06T 2210/41; G03B 42/026
See application file for complete search history.

(56) References Cited

U.S. PATENT DOCUMENTS

| | | |
|---|---|---|
| 2003/0081734 A1 | 5/2003 | Nicolas et al. |
| 2009/0168966 A1* | 7/2009 | Suzuki .................. A61B 6/032 378/116 |
| 2012/0155609 A1 | 6/2012 | Lemminger et al. |
| 2016/0073975 A1* | 3/2016 | Hefetz .................. A61B 6/037 600/427 |
| 2016/0073979 A1* | 3/2016 | Braun .................. A61B 6/467 5/601 |
| 2016/0089094 A1 | 3/2016 | Kawamura et al. |
| 2016/0213329 A1 | 7/2016 | Dirkes |
| 2017/0100089 A1 | 4/2017 | Chang et al. |
| 2017/0112456 A1 | 4/2017 | Ohga et al. |
| 2017/0119338 A1 | 5/2017 | Merckx |
| 2017/0312032 A1* | 11/2017 | Amanatullah ......... A61B 34/10 |
| 2017/0322484 A1 | 11/2017 | Erhard |
| 2018/0021000 A1 | 1/2018 | Akiyama et al. |
| 2018/0140270 A1* | 5/2018 | Profio .................. A61B 5/0555 |
| 2018/0160995 A1 | 6/2018 | Akiyama et al. |
| 2018/0182102 A1 | 6/2018 | Jerebko et al. |
| 2019/0000407 A1* | 1/2019 | Muller .................. A61B 6/482 |

FOREIGN PATENT DOCUMENTS

| | | |
|---|---|---|
| DE | 102015201070 A1 | 7/2016 |
| EP | 3387997 A1 | 10/2018 |

OTHER PUBLICATIONS

German Office Action dated Dec. 20, 2018.
European Office Action dated Nov. 12, 2019.
United States Office Action for corresponding U.S. Appl. No. 16/223,287, dated May 18, 2020.
United States Notice of Allowance for corresponding U.S. Appl. No. 16/223,287, dated Jul. 31, 2020.

* cited by examiner

METHOD AND APPARATUS FOR ENSURING CORRECT POSITIONING FOR A RADIOGRAPHY ACQUISITION

PRIORITY STATEMENT

The present application hereby claims priority under 35 U.S.C. § 119 to European patent application number EP17209022.7 filed Dec. 20, 2017, the entire contents of which are hereby incorporated herein by reference.

FIELD

Embodiments of the invention generally relate to a method and a device for positioning a body region for an acquisition by a radiography system, in particular for real-time adjustment of camera image using simulated radiography. Embodiments of the invention also generally relate to a control device for a radiography system and to a corresponding radiography system.

BACKGROUND

In radiography acquisition, the object to be acquired, for instance a knee, a wrist or an ankle, is positioned by a professional in such a way that a usable acquisition can be produced for the forthcoming examination. It often happens, however, that the orientation or positioning of the object or of the elements performing the acquisition was not optimum, with the result that the object is, for instance, offset in the acquisition, part of the object is truncated, or the object has been imaged from an incorrect acquisition angle.

The quality of the positioning has been assessed until now on the basis of the acquired X-ray image, mostly using the experience of the professional, or based on a subjective perception. If the positioning was not correct, another acquisition must be produced, which means an additional dose for the patient and more time spent for the professional. This is a disadvantage for the patient and the professional. Furthermore, every additional acquisition reduces the service life of the radiography system.

There has been no technical solution until now. A new acquisition must be performed when images are not suitable for diagnosis.

SUMMARY

At least one embodiment of the present invention defines an alternative, more convenient method and a corresponding apparatus or control device for controlling a radiography system, by which the at least one of the disadvantages described above are avoided.

Embodiments are directed to a method, an apparatus, and a control device and a radiography system.

Firstly as clarification to improve understanding of the statements to follow, within the meaning of an embodiment of the invention, a radiography system refers to a system for projection radiography and not for cross-sectional imaging (tomography). Thus X-ray radiation is beamed through regions of the body of the patient from one direction. On the opposite side, the radiation is registered by suitable materials, for instance film or a position-resolving detector, thereby producing a projection image, which is typically two-dimensional. Systems for computed tomography or corresponding systems do not constitute radiography systems within the meaning of an embodiment of the invention.

The advantages of the invention are particularly striking in the field of two-dimensional radiography acquisitions.

The method according to an embodiment of the invention for positioning a body region of a patient, which may be a person or even an animal, for a radiography acquisition, in particular a two-dimensional radiography acquisition, by a radiography system, comprises:
a) Providing an examination requirement;
b) Pre-positioning the body region;
c) Pre-positioning an acquisition unit;
d) Producing a positioning acquisition;
e) Producing a preview image; and
f) Output.

The method according to an embodiment of the invention for positioning a body region of a patient for a radiography acquisition by a radiography system, comprises:
a) providing an examination requirement for the body region;
b) pre-positioning the body region in the radiography system for the radiography acquisition;
c) pre-positioning an acquisition unit of the radiography system for the radiography acquisition;
d) producing a three-dimensional positioning acquisition of the body region using a 3D camera system;
e) producing a preview image from the three-dimensional positioning acquisition, wherein a patient model is generated from the three-dimensional positioning acquisition, and the preview image is produced from the patient model, and wherein the preview image depicts a representation as if made using the acquisition unit of the radiography system as intended in the pre-positioning adopted in step c); and
f) outputting at least one of the preview image and positioning information based on the preview image.

The apparatus according to an embodiment of the invention for positioning a body region of a patient for a radiography acquisition by a radiography system comprises:
an interface for providing an examination requirement for the body region;
an interface for pre-positioning an acquisition unit of the radiography system;
a 3D camera system for producing a three-dimensional positioning acquisition of the body region, or a data interface for receiving the positioning acquisition;
a production unit for producing a preview image from the positioning acquisition, wherein the production unit is designed to produce the preview image from a patient model generated from the positioning acquisition, wherein the preview image depicts a representation as it would be made using the acquisition unit of the radiography system; and
an output unit for outputting the preview image or positioning information based on the preview image.

In this respect, at least one embodiment is directed to a corresponding computer program product comprising a computer program, which can be loaded directly into a computing system and/or a memory device of a control device of a radiography system and which contains program segments, in order to perform all the steps of the method according to at least one embodiment the invention when the program is executed in the computing system and/or the control device. The computer program product may comprise in addition to the computer program, if applicable, extra elements such as e.g. documentation and/or extra components, including hardware components, such as e.g. hardware keys (dongles etc.) for using the software.

For transfer to the computing system and/or to the control device, and/or for storage on, or in, the computing system and/or the control device, a computer-readable medium, for instance a memory stick, a hard disk or any other portable or permanently installed data storage medium can be used, on which are stored the program segments of the computer program, which program segments can be downloaded and executed by a computing system and/or a processing unit of the control device. For this purpose, the processing unit can comprise, for example, one or more interacting microprocessors or the like.

At least one embodiment of the present invention is directed to a non-transitory computer program product comprising a computer program, directly loadable into a memory device of a control device or a memory device of a processing device, including program segments to perform the method of claim 1 when the computer program is executed via the control device or the processing device.

At least one embodiment of the present invention is directed to a non-transitory computer-readable medium, storing program segments, readable and executable by a processing unit to perform the method of claim 1 when the program segments are executed by the processing unit.

BRIEF DESCRIPTION OF THE DRAWINGS

The invention is described again below in greater detail using example embodiments and with reference to the accompanying figures. Identical components are denoted by the same reference numbers in the various figures, which are generally not shown to scale and in which.

DETAILED DESCRIPTION OF THE EXAMPLE EMBODIMENTS

Figure 1:
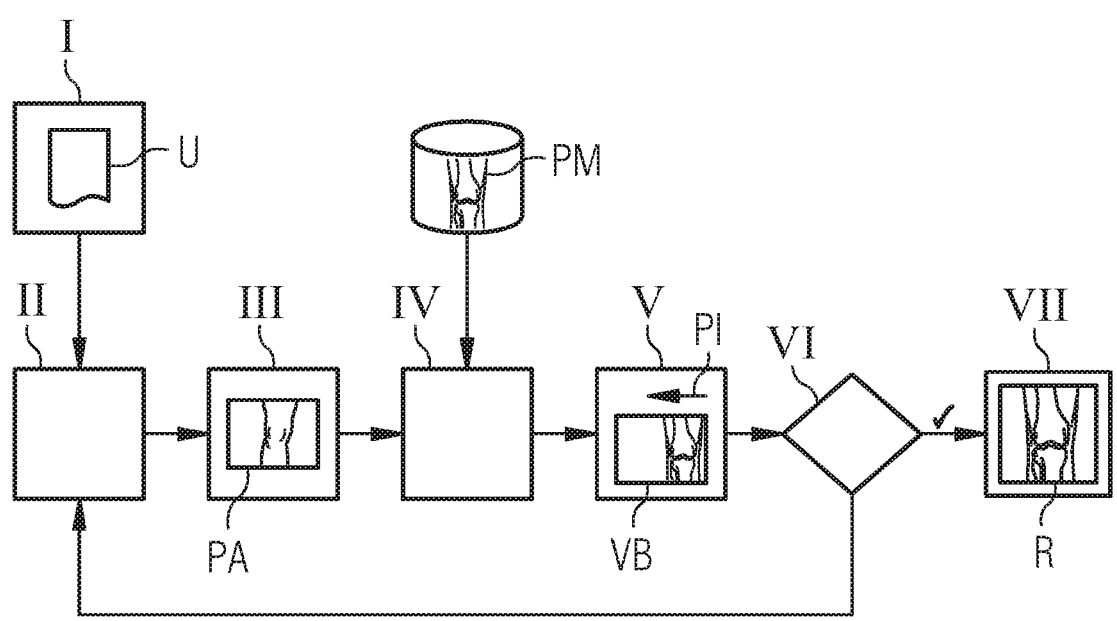
FIG. 1 is a schematic block diagram of a preferred method procedure.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

Firstly as clarification to improve understanding of the statements to follow, within the meaning of an embodiment of the invention, a radiography system refers to a system for projection radiography and not for cross-sectional imaging (tomography). Thus X-ray radiation is beamed through regions of the body of the patient from one direction. On the opposite side, the radiation is registered by suitable materials, for instance film or a position-resolving detector, thereby producing a projection image, which is typically two-dimensional. Systems for computed tomography or corresponding systems do not constitute radiography systems within the meaning of an embodiment of the invention. The advantages of the invention are particularly striking in the field of two-dimensional radiography acquisitions.

Embodiments of the invention are also confined to digital radiography systems. Preferred systems in this context are floor-mounted systems, systems having ceiling-mounted emitters, if applicable comprising table and wall-mounted grid unit, systems comprising emitter and detector on robotic support arms, or even mobile X-ray systems.

The method according to an embodiment of the invention for positioning a body region of a patient, which may be a person or even an animal, for a radiography acquisition, in particular a two-dimensional radiography acquisition, by a radiography system, comprises:

a) Providing an Examination Requirement.

In this step, the method is informed of which body region, for instance which bone or which organ, is involved and what acquisition is meant to be performed. The examination requirement may simply comprise a reference to the body region, e.g. "knee AP", knee lateral". In addition to the examination requirement, it is also possible to provide an organ program that comprises an examination requirement. The organ program is called, for instance, knee AP, but contains all the parameters needed for a specific radiography acquisition, for example information on the generator, the image processing, the image presentation and/or the device position.

b) Pre-Positioning the Body Region.

In the radiography system, the body region is pre-positioned for the radiography acquisition. For instance this is done by positioning the patient such that the body region concerned is aligned above an image detector.

c) Pre-Positioning an Acquisition Unit.

This is done by positioning the acquisition unit and, if applicable, also the image detector of the radiography system, suitably for the radiography acquisition. This positioning should be performed in accordance with the examination requirement. If the examination requirement comprises relevant control commands, or the method has access to a database containing control commands that are computationally linked to information from an examination requirement, this pre-positioning can be performed completely automatically.

d) Producing a Positioning Acquisition.

A three-dimensional positioning acquisition of the body region is produced using a 3D camera system. This 3D camera system can comprise a 3D camera, or else two cameras from which the image information is combined. The positioning acquisition is produced while the body region is in its position adopted in step b). Should the patient have moved, this can also be understood to be pre-positioning within the meaning of the invention, because it is also perfectly possible for step b) to take place before step a) or after step c).

e) Producing a Preview Image

To produce the preview image, first a patient model, for example a three-dimensional body model or bone model, is generated from the positioning acquisition. Then the preview image is produced from this patient model, for instance as a projection of a three-dimensional patient model onto a two-dimensional plane, or as a section from this patient model. The preview image depicts a representation as it would be made using the acquisition unit of the radiography system as intended in the pre-positioning adopted in step c).

The fact that the relative position of the 3D camera system relative to the acquisition unit is known, or at least can be determined or calibrated very easily, makes it possible to implement the last point, which basically constitutes a simulation of the subsequent radiography acquisition. Since these positions are known, an association can be made between the positioning acquisition and the viewing angle and field of view of the acquisition unit. From pre-positioning data for the acquisition unit and from the positioning acquisition, calculations can be used to transform this spatially so that it is presented from the viewing angle of the acquisition unit. To do this, basically only the transformation matrix for transforming the viewing direction of the 3D camera system onto the viewing direction of the acquisition unit must be known. The patient model can thereby be aligned in position and overlay automatically with the body region.

The patient model may be, for example, a physical model of the object, a form of voxel phantom having defined properties. In accordance with the acquisition geometry and acquisition parameters, X-ray quanta can be simulated, which traverse the object, where they are scattered or absorbed, and ultimately produce a projection image on the detector, e.g. by means of ray tracing or Monte Carlo simulation. During this simulation, the parameters of the X-ray quanta should match the real parameters (those for acquiring the planned radiography acquisition), in particular as regards the beam energy, the beam current and/or the kV/mAs value. It is thereby possible in particular to identify in advance overexposure or underexposure.

f) Output

In this step, the preview image and/or positioning information based on the preview image, is output. Alternatively or additionally, the preview image can be analyzed automatically to ascertain whether it represents the body region correctly in accordance with the examination requirement for the radiography acquisition.

An operator can use the preview image to decide whether the settings on the system or the pre-positionings are suitable or need to be corrected. A radiography acquisition does not need to be performed for this purpose, and the patient need not be exposed to any dose until the decision.

Alternatively or additionally, the method can also notify the operator automatically by means of the positioning information whether or not the preview image is acceptable. Particularly preferably, an automatic analysis of the preview image is used to generate the positioning information.

If powerful computers, such as are standard nowadays, are used to produce the patient model, then real-time adjustment of live camera images, which are converted in real time into simulated X-ray images, is possible as a positioning aid.

The following would be considered an alternative to steps e) and f): a database is set up in the system containing X-ray images for different system settings (projections) correlated with the camera view onto the part of the body of the patient. The camera view is the view onto a 3D avatar of the patient; i.e. specifics of the actual patient image such as clothing, hair, illumination, . . . in the room are excluded. Thus this database consists of the three parameters X-ray image, device position and camera view onto the avatar. The database grows with every radiography acquisition (in addition, X-ray images from other systems could be added to the database). If the device is now positioned and the avatar image made, it is possible to find the correlated X-ray image and display same as the preview image. The method can be improved by taking into account additional parameters: planned acquisition parameters (kV, mAs, dose, . . . ), image processing, volume of the avatar, . . . .

The apparatus according to an embodiment of the invention for positioning a body region of a patient for a radiography acquisition by a radiography system comprises the following components:

an interface for providing an examination requirement for the body region. For instance this interface can constitute a data interface to an input unit, for example a computer or simply a keyboard, via which a user can enter the examination requirement manually.

an interface for pre-positioning an acquisition unit of the radiography system. For example, this interface may control a movement unit (or send relevant control data to a control unit), which can move the acquisition unit.

A 3D camera system for producing a three-dimensional positioning acquisition of the body region, or a data interface for receiving the positioning acquisition.

A production unit for producing a preview image from the positioning acquisition, wherein the production unit is designed to produce the preview image from a patient model generated from the positioning acquisition, wherein the preview image depicts a representation as it would be made using the acquisition unit of the radiography system as intended in the pre-positioning adopted in step c).

An output unit for outputting the preview image or positioning information based on the preview image. A preferred option is that for the purpose of producing the positioning information, which comprises displayable information, or data for further automatic processing by a computer, the preview image is preferably analyzed automatically to ascertain whether it correctly represents the body region for the radiography acquisition.

Particularly preferably, the apparatus also comprises a pre-positioning display unit, which can be used to display the required positioning of the body region.

In addition, it is preferred that the apparatus comprises sensors that can measure a positioning of a body region in a radiography system. It can thereby be verified whether a body region has been suitably pre-positioned.

A 3D camera system for producing a three-dimensional positioning acquisition of the body region, or a data interface for receiving the positioning acquisition. Since a 3D camera system need not necessarily be part of the apparatus but merely its image acquisition is required as the positioning acquisition, in theory it is possible to make use of camera systems that already exist on the radiography system or in the room.

A production unit for producing a preview image from the positioning acquisition, wherein the production unit is designed to produce the preview image from a patient model generated from the positioning acquisition, wherein the preview image depicts a representation as it would be made using the acquisition unit of the radiography system as intended in the pre-positioning adopted in step c).

The apparatus preferably comprises a separate model-production unit, in which the patient model is produced. In the simplest case, generating the patient model can also be achieved by selecting from a database an appropriate patient model in accordance with the examination requirement and the relative orientation of 3D camera system and acquisition unit.

An output unit for outputting the preview image or positioning information based on the preview image. A preferred option is that for the purpose of producing the positioning information, which comprises displayable information, or data for further automatic processing by a computer, the preview image is preferably analyzed automatically to ascertain whether it correctly represents the body region for the radiography acquisition.

A control device according to an embodiment of the invention for controlling a radiography system is designed to perform a method according to the invention and/or comprises an apparatus according to an embodiment of the invention.

A radiography system according to an embodiment of the invention comprises a control device according to an embodiment of the invention.

Most of the aforementioned components and most of the apparatus or the control device can be implemented in full or in part in the form of software modules in a processor of a suitable apparatus or control device. An implementation largely in software has the advantage that even computing systems and/or control devices already in use can be easily upgraded by a software update in order to work in the manner according to an embodiment of the invention.

In this respect, at least one embodiment is directed to a corresponding computer program product comprising a computer program, which can be loaded directly into a computing system and/or a memory device of a control device of a radiography system and which contains program segments, in order to perform all the steps of the method according to at least one embodiment the invention when the program is executed in the computing system and/or the control device. The computer program product may comprise in addition to the computer program, if applicable, extra elements such as e.g. documentation and/or extra components, including hardware components, such as e.g. hardware keys (dongles etc.) for using the software.

For transfer to the computing system and/or to the control device, and/or for storage on, or in, the computing system and/or the control device, a computer-readable medium, for instance a memory stick, a hard disk or any other portable or permanently installed data storage medium can be used, on which are stored the program segments of the computer program, which program segments can be downloaded and executed by a computing system and/or a processing unit of the control device. For this purpose, the processing unit can comprise, for example, one or more interacting microprocessors or the like.

Further, particularly advantageous embodiments and developments of the invention are given in the dependent claims and in the following description, where the claims in one category of claims can also be developed in a similar way to the claims and passages of the description in another category of claims, and in particular individual features of different example embodiments or variants can also be combined to create new example embodiments or variants.

Normally the 3D camera system acquires or produces as the positioning acquisition a three-dimensional surface image of the body region. Although the patient model can theoretically be selected from a database from a set of many potential models, for instance as described above, it is preferable that a three-dimensional patient model is produced from the surface image and three-dimensional organ data objects of an organ database. The organ database preferably contains three-dimensional graphics objects, in particular from the group comprising organs, bones, cartilage, muscles, vessels, nerves and other tissues, and additionally markers, which can be used for positioning the objects in the surface image or for registering the objects with the surface image.

It is possible to calculate an avatar from the three-dimensional surface information, for instance using the machine learning principle.

The preview image is preferably then produced from a combination of the position of the pre-positioned acquisition unit and the three-dimensional patient model. This can be done, for example, by a spatial translation or rotation of the patient model in such a way that the patient model depicts a representation as though the 3D camera system were aligned identically with the acquisition position. Then a projection of the patient model in the viewing direction of the acquisition unit is preferably made.

A corresponding apparatus preferably comprises an organ database or a data interface to such an organ database, wherein the production unit is designed to produce a three-dimensional patient model from the positioning acquisition and three-dimensional organ data objects of the organ database.

The patient model is preferably produced on the basis of the machine learning principle and/or from statistical body models. It preferably has the form of a (personalized) avatar. For an optimum real-time display of a simulated X-ray image, it is advantageous to use the machine learning principle because the processing time for producing the preview image is reduced. For this purpose, a neural network must be trained in advance using a large volume of data, e.g. camera and X-ray images.

The examination requirement preferably specifies, in addition to the positioning, additional acquisition parameters for the acquisition unit, for instance energy, exposure time, collimator setting. The preview image simulates here a radiography acquisition that would have been acquired using these acquisition parameters.

The preview image is preferably displayed on a screen, for instance in the room or even remotely, or as a projection, for instance on a table top. The operator can be informed by images that are projected onto the object/into the surroundings how the setpoint position appears, or what must be done (e.g. a right-pointing arrow could indicate that the body region should be moved to the right, until an indicator goes green, for instance). The setpoint position is a position in which the preview image is acceptable and hence also subsequently the final radiography acquisition is highly likely to be acceptable. Acceptable means that a physician would consider this acquisition acceptable in terms of being of diagnostic use. In purely technical terms, an acquisition can be deemed acceptable if, for instance, the examined body region is imaged completely and is positioned correctly (e.g. for a knee acquisition, the joint cavity is visible), there is sufficient contrast in the image, there are no irrelevant regions in the radiation field, or, of fundamental importance, the correct body region is imaged (e.g. there is no left/right swap).

In theory, the patient himself can also be the operator, and can use the positioning information to perform the positioning without background knowledge.

The positioning information preferably contains information on whether or not the preview image is acceptable according to the examination requirement, and preferably also what settings should be adjusted, e.g. collimator settings or position/rotation of the display unit or of the body region.

The output is preferably implemented using a visual and/or audible indicator. It preferably contains information, in particular pictorial representations or voice commands, on how the setpoint position appears, whether the setpoint position is reached and/or navigation information.

The output preferably comprises displaying a change in a light field of the radiography system, wherein the brightness and/or color of the light field preferably changes as soon as correct positioning is achieved.

The radiography system is preferably controlled, wherein at least the steps of the method according to the invention are executed two or more times using different pre-positionings of the acquisition unit and/or of the body region. In a preferred embodiment, this repeated execution can proceed purely automatically by not moving the body region and varying automatically only the pre-positioning of the acquisition unit. Of course the pre-positioning of the detector can also be changed. The detector should always be positioned such that the beam from the acquisition unit strikes the detector. In theory, it is also possible to change the pre-positioning of the body region on its own. In this case, for example, the patient could be given automated navigation aids, for instance by a voice that announces the positioning (e.g. "further to the left") or suitable symbols, which are displayed.

The aforementioned method steps are cycled through until the positioning information indicates correct positioning of the acquisition unit in accordance with the examination requirement, and thereupon an image acquisition is produced by the acquisition unit preferably automatically.

Thus if the pre-adjustment is incorrect, a new pre-adjustment is made, or the existing pre-adjustments are modified and again a positioning acquisition is made and a preview image generated and output automatically. When the preview image is correct, the radiography acquisition can be performed.

Newly acquired images (radiography acquisitions and positioning acquisitions, or all the relevant parameters) can be added continuously to the database for a trained neural network. The assessment of the constantly re-acquired images (suitable for diagnosis, not suitable for diagnosis, or even gradations thereof) can be performed manually by professionals or automatically.

Figure 3:
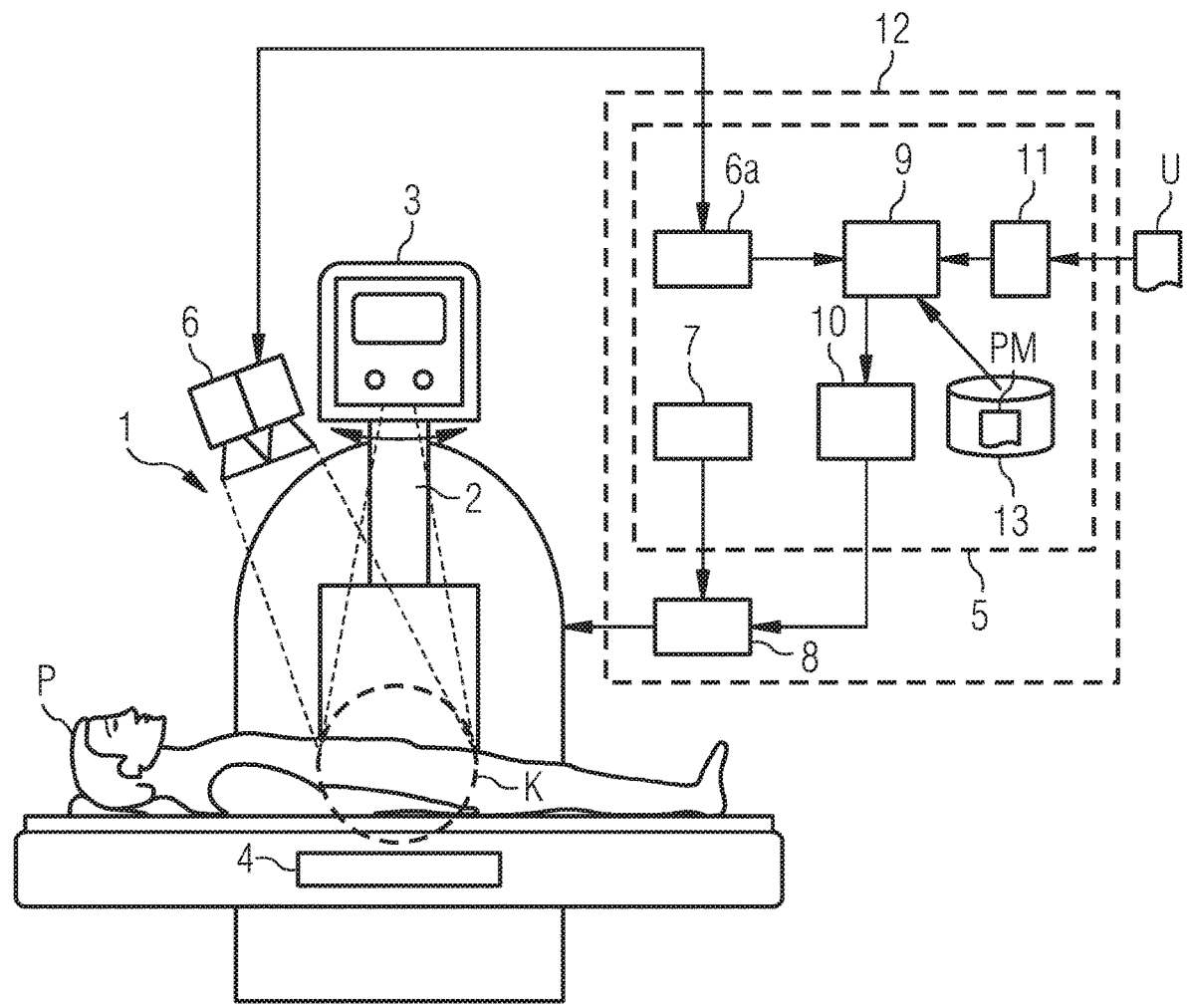
FIG. 3 is a highly simplified diagram of a preferred radiography system comprising an example embodiment of an apparatus according to the invention for performing the method.

FIG. 1 shows a schematic block diagram of a preferred method procedure for positioning a body region K of a patient P for a radiography acquisition R by a radiography system 1 (see also FIG. 3).

In step I, an examination requirement U for the body region K is provided. Here, the system is informed, for instance, of which organ is involved and what acquisition is meant to be performed. The example case in which the examination requirement U has as an objective a radiography acquisition R of the knee, is assumed below.

In step II, pre-positioning both of the body region K in the radiography system 1 and of an acquisition unit 3 of the radiography system 1 is performed for the radiography acquisition (R). In the example case, the patient is asked to place his knee in a certain position, the acquisition unit 3 is pre-positioned over the knee such that it is most likely that the knee cavity would be imaged correctly in a radiography acquisition R. Although the pre-positioning may appear correct from the outside, this may not necessarily be the case, and "dose-free" verification according to the invention is performed.

In step III, a three-dimensional positioning acquisition PA of the body region K is produced by a 3D camera system 6 while the body region K is in the position it adopted in step II. Thus a three-dimensional surface image OB of the knee is obtained in the example case. With regard to the surface image OB and producing a patient model PM, reference is made to the description relating to FIG. 2.

In step IV, a preview image VB is produced from the positioning acquisition PA. This is done by first generating a patient model PM from the positioning acquisition PA and, if applicable, also from the examination requirement U (see FIG. 2). In the example case, a three-dimensional model of the knee containing visible bones and a transparently represented skin and muscle layer is retrieved from a database and registered with the surface image OB. The resultant image then constitutes the patient model PM.

Then the preview image VB is produced, if applicable by adjusting the spatial orientation and/or positioning of the patient model PM such that it depicts a representation as it would be made using the acquisition unit 3 of the radiography system 1 as intended, which acquisition unit has been pre-positioned in step II. In the example case, a two-dimensional projection of the patient model PM is produced that appears as though it were acquired using the acquisition unit 3.

In step V, the preview image VB and positioning information PI based on the preview image VB is output. In the example case, it has been ascertained in the processing of the preview image VB by automatic image recognition that the knee would be located too far to the right in a radiography acquisition. In addition to a graphical representation of the preview image VB, an arrow is output as the positioning information PI, which indicates that the knee should be moved to the left.

In the present embodiment of the method, however, this can be corrected automatically.

In step VI, an analysis is performed to determine whether correct positioning exists. This is not the case in the example case. Therefore part of the method is repeated from step II. In the example case, rather than the knee being moved to the left, the acquisition unit is moved to the right and the steps III to VI are repeated.

If acquisition unit 3 and body region K are correctly positioned with respect to one another, a radiography acquisition is produced in step VII.

Figure 2:
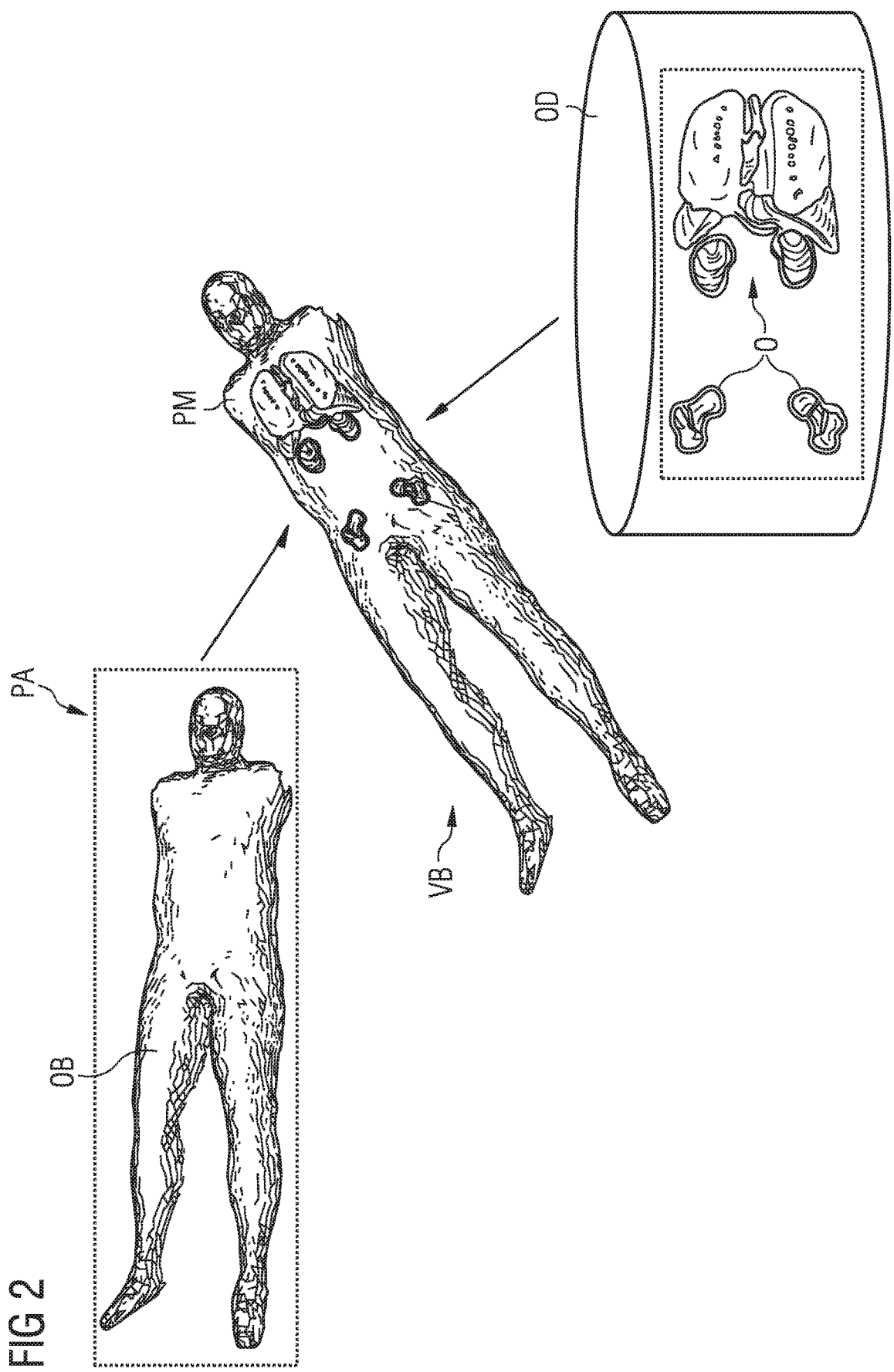
FIG. 2 is a schematic diagram of the formation of a patient model.

FIG. 2 shows a schematic diagram of the formation of a patient model PM. In the case shown, the patient model PM of an entire body is depicted. In principle, however, it is sufficient to produce merely a patient model PM of the body region K concerned, which can be inferred, for instance, from the examination requirement U. It is advantageous in this case, however, to present at least a slightly larger region in the patient model PM than is meant to be acquired ultimately in order to be able to show structures, for example organs, that may protrude into the image if movements are made and which actually should not be X-rayed.

The top box shows the positioning acquisition PA containing the surface image OB, as it might have been acquired using the 3D camera system 6 (see FIG. 3). The surface image OB merely shows the surface of the patient P without internal structures. These structures, in this case referred to as objects O, can include all possible internal structures in the body, for instance bones, organs, vessels, connective tissue or nerves. The objects here exist as three-dimensional graphics data objects in an object database OD. Organs and bones from pre-existing models, for instance from statistical body models, are preferably used. Alternatively, also three-dimensional CT datasets from comparable patients can be introduced into the patient model PM (into the avatar).

In order to produce the patient model PM, the objects are fitted into the three-dimensional surface image, for instance by way of graphical registration.

This patient model PM forms the basis for producing the preview image VB. In the simplest case, the preview image VB may be the depiction of the patient model PM, but it is more advantageous if the preview image VB in its way is similar to, or even identical to, the representation of the planned radiography acquisition R. The preview image VB is preferably calculated from the patient model PM by simulating an X-ray projection image that would be obtained on the basis of the positioning of acquisition unit 3 and detector 4 with respect to the body region K and on the basis of the set parameters such as beam energy, collimator, etc. for instance. It is therefore preferable that the preview image VB is a two-dimensional projection of the three-dimensional patient model PM having a transparent surface image OB.

In the following explanations it is assumed that the radiography system 1 is a digital X-ray apparatus. In principle, however, the method can also be used on other radiography systems 1.

FIG. 3 shows in a highly simplified diagram a radiography system 1 having a control device 12 for performing the method according to an embodiment of the invention. The radiography system 1 comprises, as is standard practice, an acquisition unit 3, which here constitutes an X-ray source and which during a radiography acquisition (R) beams radiation through a patient (P), with the result that the radiation strikes a detector 4 opposite the acquisition unit 3. A movement mechanism 2, in this case a pivoting arm, can be used to move the acquisition unit 3, e.g. to raise/lower, tilt or rotate the acquisition unit. Typically the movement mechanism 2 allows a plurality of different movements, so that the acquisition unit can be moved optimally in terms of its height, lateral position and angle of inclination.

For the control device 12, only those components are shown that are essential to explaining an embodiment of the invention. Conventional radiography systems and associated control devices generally are known to a person skilled in the art and therefore need not be explained in detail.

The radiography system 1 can be controlled by the control device 12 via a control interface 8, i.e. for instance the movement mechanism 2 is controlled to move the acquisition unit 3, or a radiography acquisition is started. The acquisition unit 3 can also be adjusted via the control interface 8, for example with regard to the exposure time or the beam energy.

A user interface, an acquisition interface for the acquired image data or an image-data reconstruction unit are not shown even though the control unit 12 may obviously comprise such elements as well.

The control device 12 comprises an apparatus 5 for positioning a body region K of a patient P for a radiography acquisition R. In the case shown, this apparatus 5 does not act directly on the radiography system 1 but via the control interface 8 of the control device 12.

The apparatus 5 comprises an interface 11 for providing an examination requirement U for the body region K. In the case shown, it receives an examination requirement U from outside, which can be entered, for instance, via a user interface. It is entirely possible to make use of a user interface of the control device 12 for this purpose.

Pre-positioning of an acquisition unit 3 of the radiography system 1 can be achieved via a further interface 7. In this case, the interface 7 sends the data for positioning to the control interface 8 of the control device 12, and this controls the movement mechanism 2 and thereby positions the acquisition unit 3 according to the information from the interface 7.

In the case shown, a 3D camera system 6 is not part of the apparatus 5, although this can certainly be the case in an alternative embodiment. Here, however, for the purpose of producing a positioning acquisition PA of the body region K, the apparatus 5 accesses a 3D camera system 6 via a camera interface 6a, controls the operation of the camera system, starts an acquisition and receives the three-dimensional positioning acquisition PA from the camera system.

This positioning acquisition PA is then provided to the production unit 9, as is the examination requirement U, which is provided by means of the interface 11 of the production unit 9. A patient model PM is generated according to the positioning acquisition PA and, if applicable, also according to the examination requirement U, by being suitably selected from a database 13, which here is optionally part of the apparatus 5.

In addition, a preview image VB is produced by means of the production unit 9 and the generated patient model PM, which preview image depicts a representation as it would be made using the acquisition unit 3 of the radiography system 1 as intended. This can be achieved, for example, by first producing a three-dimensional patient model PM, performing a spatial translation or rotation of this patient model according to the position of the 3D camera system relative to the acquisition unit 3, and then making a projection of the patient model. Alternatively, it is obviously also possible to adjust the projection direction accordingly. In the case shown, in which the 3D camera system is both offset and tilted with respect to the acquisition unit 3, the patient model PM, for instance, could be spatially oriented in such a way that it would be as though it were acquired by the 3D camera system at the location of the acquisition unit 3. A suitable preview image can be produced therefrom from a corresponding vertical projection.

The preview image VB and/or positioning information PI based on the preview image VB can be output via an output unit 10. The output unit 10 may thus be a display or an interface for data exchange with a computer. In the case shown here, the output unit 10 is designed (also) to send data to the control interface 8 and thereby, for instance, to achieve further pre-positioning of the acquisition unit 3.

Finally it should be reiterated that the method described in detail above and the presented devices or apparatuses are merely example embodiments, which can be modified by a person skilled in the art in many different ways without departing from the scope of the invention. In addition, the use of the indefinite article "a" or "an" does not rule out the possibility of there also being more than one of the features concerned. Likewise, the terms "unit" and "module" do not exclude the possibility that the components in question consist of a plurality of interacting sub-components, which may also be spatially distributed if applicable.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCES 1 radiography system
2 movement mechanism
3 acquisition unit
4 detector
5 apparatus
6 3D camera system
6a camera interface
7 interface
8 control interface
9 production unit
10 output unit
11 interface
12 control device
13 database
K body region
OB surface image
OD object database
P patient
PA positioning acquisition
PI positioning information
PM patient model
R radiography acquisition
U examination requirement
VB preview image
I-VII method steps

The invention claimed is:

1. A method for positioning a body region of a patient for a radiography acquisition by a radiography system, the method comprising:
   providing an examination requirement for the body region;
   pre-positioning the body region in the radiography system for the radiography acquisition;
   pre-positioning an acquisition unit of the radiography system for the radiography acquisition;
   producing a three-dimensional positioning acquisition of the body region using a 3D camera system, the three-dimensional positioning acquisition being a three-dimensional surface image of the body region;
   producing a preview image from the three-dimensional positioning acquisition, wherein a patient model is generated from the three-dimensional positioning acquisition and the preview image is produced from the patient model, the preview image depicts a preview of an image generated by the acquisition unit, the patient model being a three-dimensional patient model produced from the three-dimensional surface image and three-dimensional organ data objects of an organ database, the three-dimensional organ data object positioned based on the three-dimensional surface image; and
   outputting at least one of the preview image and positioning information based on the preview image.

2. The method of claim 1, wherein the patient model is produced based upon at least one of a machine learning model and a statistical body model.

3. The method of claim 2, wherein the patient model has a form of an avatar.

4. The method of claim 1, wherein the examination requirement specifies additional acquisition parameters for the acquisition unit, and the preview image simulates a radiography acquisition using these acquisition parameters.

5. The method of claim 1, wherein the preview image is displayed on a screen or as a projection.

6. The method of claim 1, wherein the positioning information contains information on settings to be adjusted and whether the preview image is acceptable according to the examination requirement.

7. The method of claim 6, wherein the positioning information contains information indicating what settings should be adjusted.

8. The method of claim 1, wherein the outputting at least one of the preview image and positioning information uses at least one of a visual indicator and an audible indicator.

9. The method of claim 8, wherein the positioning information contains at least one of information on how a setpoint position appears, navigation information, and information indicating whether the setpoint position is reached.

10. The method of claim 1, wherein the outputting at least one of the preview image and positioning information includes displaying a change in a light field of the radiography system, wherein at least one of brightness and color of the light field changes based on correct positioning.

11. The method of claim 1, the method further comprising:
   determining a correct position of the acquisition unit based on the examination requirement, and
   producing a radiography acquisition by the acquisition unit,
   wherein the determining the correct position includes performing the method of claim 1 at least one time, and at least one of the body region and acquisition unit are in a different position each performance of the method of claim 1.

12. A non-transitory computer program product comprising a computer program, directly loadable into a memory device of a control device or a memory device of a processing device, including program segments to perform the method of claim 1 when the computer program is executed via the control device or the processing device.

13. A non-transitory computer-readable medium, storing program segments, readable and executable by a processing unit to perform the method of claim 1 when the program segments are executed by the processing unit.

14. The method of claim 1, wherein the preview image is produced using a combination of the position of the pre-positioned acquisition unit and the three-dimensional patient model.

15. The method of claim 1, wherein the examination requirements includes parameters for the acquisition unit, the 3D camera system, the preview image, and a position of the acquisition unit.

16. An apparatus for positioning a body region of a patient for a radiography acquisition by a radiography system, comprising:
   an interface configured to provide an examination requirement for the body region;
   an interface configured to pre-position an acquisition unit of the radiography system;
   at least one of a 3D camera system configured to produce a three-dimensional positioning acquisition of the body region, and a data interface to receive the three-dimensional positioning acquisition, the three-dimensional positioning acquisition being a three-dimensional surface image of the body region;
   a production unit configured to produce a preview image from the three-dimensional positioning acquisition, the production unit being configured to produce the preview image from a patient model generated from the three-dimensional positioning acquisition, the preview image depicts a preview of an image generated by the acquisition unit, the patient model being a three-dimensional patient model produced from the three-dimensional surface image and three-dimensional organ data objects of an organ database, the three-dimensional organ data objects positioned based on the three-dimensional surface image; and
   an output unit configured to output at least one of the preview image and positioning information based on the preview image.

17. A control device comprising the apparatus of claim 16.

18. A radiography system comprising the control device of claim 17.

19. The apparatus of claim 16, wherein the output unit is further configured to perform automatic analysis of the preview image to ascertain whether the preview image correctly represents the body region for the radiography acquisition.

* * * * *